United States Patent [19]

Quinlan

[11] 4,442,086
[45] Apr. 10, 1984

[54] DIETHYLCARBAMAZINE RESINATE AND STYRYLPYRIDINIUM RESINATE-DIETHYLCARBAMAZINE RESINATE EDIBLE ANTHELMINTIC TABLETS FOR COMPANION ANIMALS

[75] Inventor: James M. Quinlan, Trenton, N.J.

[73] Assignee: American Cyanamid Company, Stamford, Conn.

[21] Appl. No.: 239,966

[22] Filed: Mar. 3, 1981

Related U.S. Application Data

[63] Continuation-in-part of Ser. No. 60,931, Jul. 26, 1979, abandoned.

[51] Int. Cl.$^3$ .............................................. A61K 31/74
[52] U.S. Cl. ...................................................... 424/79

[58] Field of Search ...................................... 424/78, 79

[56] References Cited

U.S. PATENT DOCUMENTS

| | | | |
|---|---|---|---|
| 3,177,116 | 4/1965 | Wood et al. | 424/263 |
| 3,179,559 | 4/1965 | Wood et al. | 424/263 |
| 3,250,623 | 5/1966 | Clair et al. | 424/79 |
| 3,862,312 | 1/1975 | Rimington et al. | 424/79 |

Primary Examiner—Frederick E. Waddell
Attorney, Agent, or Firm—E. J. Tsevdos; H. G. Jackson

[57] ABSTRACT

There are provided palatable anthelmintic resinate compositions for companion animals, containing anthelmintically effective amounts of a styrylpyridinium compound and/or an N,N-dialkylpiperazine carboxamide.

4 Claims, No Drawings

DIETHYLCARBAMAZINE RESINATE AND STYRYLPYRIDINIUM RESINATE-DIETHYLCARBAMAZINE RESINATE EDIBLE ANTHELMINTIC TABLETS FOR COMPANION ANIMALS

This application is a continuation-in-part of Ser. No. 060,931, filed July 26, 1979, now abandoned.

SUMMARY OF THE INVENTION

The present invention relates to palatable acidic resinate compositions which contain a styrylpyridinium compound and/or an N,N-dialkylpiperazine carboxamide and find utility as palatable anthelmintic compositions for the treatment of helminthiasis in companion animals.

Styrylpyridinium compounds and methods for their preparation are disclosed in U.S. Pat. Nos. 3,177,116 and 3,179,559, issued Apr. 6, 1965 and Apr. 20, 1965, respectively. These patents are incorporated herein by reference. Similarly, N,N-dialkylpiperazine carboxamides are disclosed in U.S. Pat. No. 2,467,895, issued Apr. 19, 1949. This patent is incorporated herein by reference. The above-identified compounds are known to be useful for combatting helminthiasis in domestic animals. They are said to be effective when administered by the oral route. Administration of both the N,N-dialkylpiperazine carboxamides and the styrylpyridinium halides, in the form of capsules, tablets and in the feed, is contemplated by the patentees. However, it has been found that the styrylpyridinium compounds are unpalatable when taken orally and the N,N-dialkylpiperazine carboxamides are only partially acceptable to companion animals when administered in a form in which the active compound is permitted to come in contact with the animals taste buds. Over the years, veterinarians have continually complained that the available tablets, pills or formulated compositions marketed for admixture of the styrylpyridinium halides with feeds is unsatisfactory and has resulted in the reluctance of the animals to ingest the medicated feed, tablets or pills. It would therefore be highly advantageous and most desirable if the above-named compounds could be rendered palatable without destroying their efficacy. Furthermore, it would be most advantageous if a palatable composition, containing a N,N-dialkylpiperazine carboxamide, alone or in combination with a styrylpyridinium compound such as a 1-methyl-2-(p-chlorostyryl) pyridinium salt, could be prepared in the form of a chewable tablet, pill, granulated product or the like.

Heretofore, it has been stated that, "both olfaction and taste are involved in canine food preferences". Thus, the use of split plate evaluations for preference are crucial in delineating olfactory medicated preferences. Actual consumption of an article is a function of combined odor and taste acceptability which is herein interpreted as palatability.

It is, therefore, an object of this invention to provide palatable, therapeutically effective compositions, containing a N,N-dialkylpiperazine carboxamide alone or in combination with a styrylpyridinium compound, useful for the treatment of helminthiasis in companion animals.

It is also an object of the present invention to provide methods for preparing diethylcarbamazine and/or styrylpyridinium compositions which are palatable and stable when admixed with animal feed stuffs.

The present invention accomplishes these objectives by the provision of novel resinates of N,N-dialkylpiperazine carboxamide compounds having the formula:

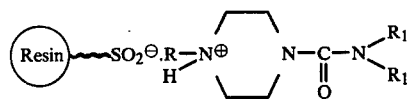

where R is hydrogen or $C_1$–$C_6$ alkyl and $R_1$ is alkyl $C_1$–$C_5$; and of styrylpyridinium compounds having the formula:

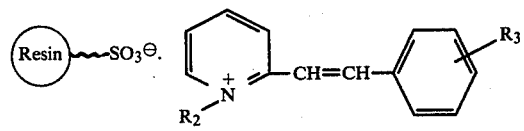

wherein $R_2$ is $C_1$–$C_4$ alkyl and $R_3$ is hydrogen or halogen.

The above compounds are described in U.S. Pat. No. 2,467,895 issued Apr. 19, 1949 and U.S. Pat. No. 3,177,116 issued Apr. 6, 1965; however, no mention is made by the patentees of resinate forms of said compounds or the improved palatability obtained with said forms.

The resinates of the above-identified compounds are prepared by reacting the free base or pharmacologically acceptable salt of the N,N-dialkylpiperazine carboxamide or the pharmacologically acceptable salt of the styrylpyridinium compound with an acidic cationic exchange resin under conditions whereby said compound becomes ionically bound to the acidic anion of the resin.

The diethylcarbamazine and/or the styrylpyridinium compound is bonded to the resin with sufficient ionic strength to withstand ionization in the mouths of animals. However, the efficacy of these anthelmintic agents is retained since the active compound is released from the resin in the stomach and/or intestinal tract of the animal after being swallowed.

In the practice of the invention, the thus prepared resinates are then admixed with from 18% to 60% by weight of desiccated granular or powdered liver, but preferably granular liver; 0% to 40% by weight of Brewer's yeast; 23.95% to 31% by weight of microcrystalline cellulose; 0% to 7% by weight of stearic acid; 0% to 0.05% by weight sodium aluminum silicate of silicon dioxide; 2% to 5% by weight of diethylcarbamazine resinate and from 0% to 7% by weight of a styrylpyridinium resinate; said resin employed in the preparation of said resinates having a particle size of less than 800μ and preferably an average particle size between about 45μ and 300μ. Said ion exchange resin being further characterized as a strongly acidic high capacity sulfonic cation exchange resin preferably of the polystyrene divinylbenzene type having from 4% to about 8% cross linkage.

When the compositions of the present invention are prepared using only the N,N-dialkylpiperazine carboxamide as the anthelmintic agent, the essential active ingredients of the compositions are 2% to 5% by weight of the N,N-dialkylpiperazine carboxamide resinate, preferably a high capacity sulfonic cationic exchange resin of the polystyrene-divinylbenzene type, and 18% to 60% by weight of desiccated liver.

When two anthelmintic agents are employed in the compositions of the invention, the essential active ingredients are 2% to 5% by weight of the N,N-dialkylpiperazine carboxamide; 3% to 7% by weight of the styrylpyridinium resinate and 18% to 60% by weight of desiccated liver.

Diluents such as pharmaceutically acceptable binding agents, lubricants and the like, which are in the manufacture of the compositions of the invention are, hereinafter, described.

Preferred compositions comprise about 3% by weight of diethylcarbamazine resinate, about 5% by weight of 1-methyl-2-(p-chlorostyryl)pyridinium resinate, about 55% to 58% by weight of desiccated liver, about 30% by weight of microcrystalline cellulose, and about 3% to 7% by weight of stearic acid. The said resinates being high capacity sulfonic cationic exchange resins of the polystyrene divinylbenzene type with an average particle size in the range of from $45\mu$ to $300\mu$.

Another preferred composition comprises about 3% by weight of diethylcarbamazine resinate, 5% by weight of 1-methyl-2-(p-chlorostyryl)pyridinium resinate, 18% to 44% by weight of desiccated liver, 37% to 18% Brewer's yeast, 30% by weight of microcrystalline cellulose, and 3% to 7% by weight of stearic acid.

Still another preferred composition comprises 3% by weight of diethylcarbamazine, 40% by weight of Brewer's yeast, 20% by weight of granular liver, 30% by weight of microcrystalline cellulose, and 7% by weight of stearic acid.

Preparation of the diethylcarbamazine resinate and styrylpyridinium resinate can be achieved by admixing the diethylcarbamazine compound with deionized water or the styrylpyridinium compound with an alcohol deionized water mixture and intimately contacting the resulting mixture with a high capacity, sulfonic acid cationic exchange resin having a 4% to 8% divinylbenzene cross-linkage and a screen size of about 16 to 50 mesh. The thus prepared resinate is then separated from the supernatant liquid and washed repeatedly with deionized water until the wash water has a pH of about 4.5. The resin is then dried and ground or milled to at least about $800\mu$ and preferably to an average particle size between $45\mu$ and $300\mu$. The resinates, thus prepared, can be used separately to formulate edible tablets or they may be admixed to prepare edible tablets containing both compounds.

In the preparation of the above-mentioned resinates, alcohols such as methanol, ethanol, propanol, isopropanol, butanol, isobutanol, pentanol-1, or pentanol-2, may be employed.

Strongly acidic resins are preferred in the preparation of the resinates of this invention since they provide resinates in which the diethylcarbamazine and/or styrylpyridinium compounds are more strongly bonded to the ion exchange resin to substantially prevent the compounds ionizing in the mouth of the animal to which they are fed. Among the preferred strongly acidic resins are sulfonated polystyrenes prepared from styrene and divinylbenzene which functions as a cross-linking agent. These resins include AMBERLITE® IR-120, and DOWEX® 50 and 50W. Sulfonated phenolic resins, may also be used and may include AMBERLITE® IR-1; cellulose alkylsulfonic acid resins such as CELLEX SE resin and the like may also be utilized in the preparation of the resinates of this invention.

The reaction to form the resinates can be carried out over a wide temperature range so long as the solvent remains fluid and is not evaporated in excessive amounts. For example, the reactions may be conducted at a temperature between about 0° and 100° C. and preferably at from about 20° to 50° C.

The diethylcarbamazine or styrylpyridinium solution can be contacted with the resin in any convenient manner such as by mixing the solution with the finely divided resin or by passing the solution of the anthelmintic agent through a resin bed. The molar ratio of anthelmintic agent to resin employed is not critical and is usually within the range of 0.125:1 to 3:1, preferably 0.5:1 to 2:1. A ratio within the preferred range permits efficient loading of the resin within a reasonable period of time. The anthelmintic resinates obtained in accordance with this invention contain about 10% to 60% by weight of anthelmintic and preferably about 40% to 55% of said anthelmintic. The resinate compositions can be prepared by either a batch or a continuous process and if desired both the diethylcarbamazine and styrylpyridinium compound may be loaded on a single resin. However, it is essential that in this arrangement the styrylpyridinium be loaded first and then the loaded resin thoroughly washed before the diethylcarbamazine is loaded on the resin. In this practice the resin is loaded only to about 25% to 33% by weight with the styrylpyridinium, determined on the basis of the dry weight on the resin, and then with about 13% to 18% by weight with diethylcarbamazine, determined on the basis of the dry weight of the resin. The preferred loading ration of styrylpyridinium to diethylcarbamazine or sequentially loaded resins is about 1.7 to 1. However, ratios as low as 1.3 to 1 can be used.

The sequentially loaded resinate, containing both the N,N-dialkylpiperazine carboxamide and the styrylpyridinium compound, may be illustrated as follows:

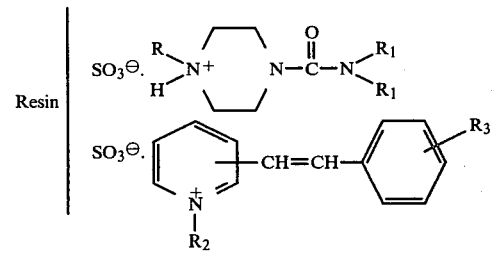

where R, $R_1$, $R_2$ and $R_3$ are as described above.

Other embodiments and advantages of this invention will become more apparent from the examples set forth below. These examples are provided for the purpose of demonstrating the invention and are not intended to limit the scope hereof.

EXAMPLE 1

Preparation of Diethylcarbamazine Resinates and Styrylpyridinium Resinates

Diethylcarbamazine Resinate

Diethylcarbamazine (1125 kg real, 5.653 kg mole) also named N,N-diethyl-4-methyl-1-piperazinecarboxamide, is charged to 2240 liters of deionized water and agitated to dissolve it. To this solution is then added a high capacity sulfonic cation exchange resin of the polystyrene divinylbenzene type (2380 kg) AMBERLITE IR-120® manufactured by Rohm & Haas Co.. The reaction slurry is filtered, washed with deionized water (2240 liters), and dried at 80°–90° C. The dried diethylcarbamazine resinate (2380 kg) which assays 45.0% diethylcarbamazine free base is then milled to −30 mesh particle size.

The above-mentioned cation exchange resin has a density of 0.85 g/cc apparent, 1.26 g/cc true; water content 44–48%; exchange capacity of 4.40 milliequivalents/g dry and a screen size of from 16 to 50 mesh.

Styrylpyridinium Resinate

A 3960 gram quantity of a sulfonic acid divinylbenzene resin (H+form) calculated to contain 1500 grams or 7.620 equivalents capacity of dry resin is mixed with a solution containing 2074 grams of 1-methyl-2-(p-chlorostyryl)-pyridinium chloride, 3000 ml of methanol and 3900 ml of deionized water. The mixture is diluted to 11,000 ml with deionized water and then allowed to settle and the supernatant liquid separated from the mixture by filtration. This washing treatment is repeated 10 times. The pH of the final wash is 4.50 and the pH of the deionized water is 4.85. The resinate is then dried at 75° C. for 48 hours and weighs 2,739 grams. The resinate passes through a 20 mesh screen and assays 52.38% 1-methyl-2-(p-chlorostyryl)-pyridinium as the chloride and has a KF moisture content of 1.305%. The resin used in the above preparation is marketed under the tradename Powdex by the Graver Water Conditioning Co., N.Y., N.Y. and is essentially 20–50 mesh material.

EXAMPLE 2

Preparation of Diethylcarbamazine Resinate

A mixture of 20–50 mesh washed Powdex resin (1667 g wet resin, calculated to contain 698.0 g dry resin or 3.546 equivalents capacity) and 500 ml of deionized water are mixed in a vessel. To this mixture is added 719.28 g (706.6 g, real; 3.546 moles) of diethylcarbamazine base. The mixture is stirred for 4 hours and then filtered and washed repeatedly with deionized water. The resinate is collected and dried at 85° C. for 24 hours. The dried resinate weighs 1389 g and assays 50.59% and 50.30% diethylcarbamazine base.

EXAMPLE 3

Preparation of Diethylcarbamazine Resinate-Edible Tablets

Diethylcarbamazine resinate (71.28 kg 3.24% w/w) prepared in accordance with the procedure of Example 1 above is blended with 1.10 kg of colloidal silicon dioxide. Brewer's yeast 873.62 kg (39.71% w/w) is passed through a 30 mesh screen and blended with the prepared diethylcarbamazine mixture. The resulting mixture is then admixed with 660.00 kg of microcrystalline cellulose. The mixture is passed through a 30 mesh screen, blended with 154.00 kg of stearic acid, 440.00 kg of dessiccated, granular, liver (20% w/w) and compacted into 2.20 g tablets using a commercial tableting machine.

EXAMPLE 4

Preparation of Diethylcarbamazine Resinate-Edible Tablets

Diethylcarbamazine resinate (71.2 kg 3.24% w/w) prepared in accordance with example 3 is admixed with 0.44 kg of sodium aluminum silicate. Desiccated, powdered, liver (444.0 kg 20.0% w/w) is then passed through a 30 mesh screen and blended with the previously prepared resinate mixture and to this mixture is added 874.28 kg (34.94% w/w) of Brewer's yeast, 660.00 kg of microcrystalline cellulose and 1540.00 kg of stearic acid. The thus prepared mixture is thoroughly blended and then formed into 2.20 g tablets using a commercial tableting machine.

EXAMPLE 5

Preparation of diethylcarbamazine resinate-styrylpyridinium resinate edible tablets Diethylcarbamazine resinate (71.28 kg 3.24% w/w) and 1-methyl-2-(p-chlorostyryl)-pyridinium resinate (104.94 kg 4.77% w/w) prepared in accordance with Example 1 are blended with 1.1 kg of colloidal silicon dioxide. Desiccated-granular liver (440.0 kg 20.0% w/w) is screened through a 30 mesh screen and admixed with the resinate mixture. Brewer's yeast (768.68 kg 34.94% w/w) is then passed through a 30 mesh screen and mixed with the previously prepared resinate mixture. Microcrystalline cellulose (660.00 kg) and 154.00 kg of stearic acid are blended with the above-noted mixture and the resulting formulation formed into 2.2 g tablets using a commercial tableting machine.

EXAMPLE 6

Palatability Evaluation of Styrylpyridinium Diethylcarbamazine edible tablets

The following tests are conducted to determine comparative acceptablility of various formulations of tablets containing 1-methyl-2-(p-chlorostyryl)-pyridinium resinate and diethylcarbamazine resinate.

Twenty adult purebred English Pointers are used in these evaluations. The dogs are housed individually in outside pens. Each pen is 4 feet wide, 10 feet long and is provided with an attached house. Pointers are used for this test because of their organoleptic sensitivity to differences between products.

Each dog is tested for intestinal parasites by a flotation method using sodium nitrate solution and Fecasol ® kits. Dog 7 is found to have a slight infestation of *Toxascaris leonina* and Dog 12 a ruminant parasite. Both infestations are gone after 14 days.

Tests for Dirofilariasis are conducted using Knott's technique and all blood samples are free of microfilaria.

In the tests each dog is fed, ad libitum, commercial dry dog food in self-feeders, and fresh, clean, water is available at all times.

A double choice format is employed with each dog being offered two choices of tablet formulations simultaneously to determine acceptability preference.

The feed containers used are rectangular plywood sheets, 24 by 31 cm, 2 cm thick, with routed depressions, 3.7 cm in diameter and 1.1 cm deep.

Each dog is offered two tablets each morning and again late afternoon for four days. Presentation is altered each time by turning the containers 180° before placing it in the cage. Time of acceptance is noted for each proffering. The container is left in the cage 30 minutes if the tablets are not readily consumed.

All dogs are less than 4 years of age and weigh between 35 and 52 pounds. The sex, habitus and initial and final weights of each dog are recorded and reported below. Also reported are the findings obtained in this test along with formulation used.

TABLE I

English Pointers used in this test

| Pen | Sex | Habitus | Initial weight lbs. | Final weight lbs. |
|---|---|---|---|---|
| 1 | F | muscular | 48 | 43 |
| 2 | F | light | 35 | 43 |
| 3 | F | light | 38 | 35.5 |
| 4 | F | muscular | 49 | 46 |
| 5 | F | light | 37 | 35.5 |
| 6 | F | fat | 49 | 47.5 |
| 7 | F | light | 39 | 39 |
| 8 | F | average | 41.5 | 43 |
| 9 | F | muscular | 46 | 42.5 |
| 10 | F | light | 40.5 | 40 |
| 11 | M | average | 45 | 42.5 |
| 12 | F | fat | 49.5 | 50 |
| 13 | M | muscular | 52 | 50 |
| 14 | F | light | 37 | 36 |
| 15 | M | muscular | 52.5 | 50.5 |
| 16 | F | average | 40 | 39 |
| 17 | M | muscular | 50 | 50.5 |
| 18 | F | light | 37 | 38.5 |
| 19 | F | average | 45 | 43 |
| 20 | F | light | 38 | 38.5 |

First Preference Test Results For Styrylpyridinium-Diethylcarbamazine Resinate Tablets Comparisons:

| Dog # | A | B | B | C | A | D | B | E | F | G | G | H |
|---|---|---|---|---|---|---|---|---|---|---|---|---|
| 1 | 2 | 3 | 7 | 2 | 8 | 1 | 8 | 2 | 5 | 5 | 3 | 7 |
| 2 | 3 | 6 | 6 | 3 | 4 | 5 | 6 | 4 | 5 | 5 | 4 | 6 |
| 3 | 5 | 5 | 7 | 3 | 7 | 3 | 10 | 0 | 5 | 4 | 3 | 7 |
| 4 | 2 | 8 | 7 | 3 | 7 | 3 | 4 | 6 | 2 | 8 | 6 | 4 |
| 5 | 3 | 6 | 5 | 5 | 5 | 5 | 1 | 9 | 3 | 7 | 4 | 6 |
| 6 | 7 | 3 | 8 | 2 | 5 | 5 | 6 | 4 | 6 | 4 | 5 | 5 |
| 7 | 4 | 6 | 4 | 6 | 9 | 1 | 5 | 5 | 6 | 4 | 5 | 5 |
| 8 | 5 | 5 | 7 | 3 | 8 | 2 | 7 | 3 | 6 | 4 | 4 | 6 |
| 9 | 4 | 6 | 5 | 5 | 10 | 0 | 6 | 4 | 5 | 5 | 6 | 4 |
| 10 | 5 | 5 | 5 | 5 | 6 | 4 | 5 | 5 | 5 | 5 | 6 | 4 |
| 11 | 4 | 6 | 7 | 3 | 8 | 2 | 4 | 6 | 4 | 6 | 5 | 5 |
| 12 | 3 | 7 | 4 | 6 | 7 | 3 | 6 | 4 | 5 | 5 | 7 | 3 |
| 13 | 6 | 4 | 4 | 6 | 5 | 5 | 5 | 5 | 6 | 4 | 5 | 5 |
| 14 | 2 | 8 | 4 | 6 | 7 | 3 | 5 | 5 | 7 | 3 | 4 | 6 |
| 15 | 6 | 4 | 5 | 5 | 7 | 3 | 8 | 2 | 2 | 7 | 7 | 2 |
| 16 | 5 | 5 | 6 | 4 | 5 | 5 | 5 | 5 | 5 | 5 | 5 | 5 |
| 17 | 5 | 5 | 6 | 4 | 4 | 6 | 8 | 2 | 6 | 0 | 2 | 3 |
| 18 | 4 | 6 | 5 | 5 | 6 | 3 | 5 | 5 | 6 | 4 | 7 | 3 |
| 19 | 6 | 4 | 4 | 6 | 10 | 0 | 8 | 2 | 4 | 6 | 7 | 3 |
| 20 | 4 | 6 | 6 | 4 | 9 | 1 | 6 | 4 | 6 | 4 | 3 | 7 |
| Totals: (Selected First) | 85 | 108 | 112 | 86 | 137 | 60 | 118 | 82 | 99 | 95 | 98 | 96 |

Tablet Compositions % w/w

A = 
- 36.36% Desiccated liver
- 18.18% Brewer's yeast
- 30.67% Microcrystalline cellulose
- 2.92% Diethylcarbamazine resinate
- 7.00% Stearic acid
- 4.87% 1-methyl-2-,(p-chlorostyryl)-pyridinium resinate
  Resinate particle size 300–800μ
- 4% Sulfonic acid-divinylbenzene cross linkage B = 
- 54.55% Desiccated liver
- 30.66% Microcrystalline cellulose
- 4.87% 1-methyl-2-(p-chlorostyryl)-pyridinium resinate
- 2.92% Diethylcarbamazine resinate
- 7.00% Stearic acid
  Resin particle size 300–800μ
- 4% Sulfonic acid-divinylbenzene cross linkage C = 
- 36.36% Brewer's yeast
- 18.18% Desiccated liver
- 30.67% Microcrystalline cellulose
- 4.87% 1-methyl-2-(p-chlorostyryl)-pyridinium resinate
- 2.92% Diethylcarbamazine resinate
- 7.00% Stearic acid
  Resin particle size 300–800μ
- 4% Sulfonic acid-divinylbenzene cross linkage D = Filarabits - Commercial edible formulation of Diethylcarbamazine E = 
- 36.36% Brewer's yeast
- 18.18% Desiccated powdered liver
- 5.19% 1-methyl-2-(p-chlorostyryl)-pyridinium resinate
- 3.01% Diethylcarbamazine resinate
- 30.26% Microcrystalline cellulose
- 7.00% Stearic acid
  Resin particle size 147–300μ
- 4% Sulfonic acid-divinylbenzene cross linkage F = 
- 35.8% Brewer's yeast
- 18.0% Desiccated powdered liver
- 5.97% 1-methyl-2-(p-chlorostyryl)-pyridinium resinate
- 3.18% Diethylcarbamazine resinate
- 0.05% Colloidial Silicon Dioxide
- 30.00% Microcrystalline cellulose
- 7.00% Stearic acid
  Resin particle size 147–300μ
- 4% Sulfonic acid-divinylbenzene cross linkage G = 
- 36.77% Brewer's yeast
- 18.0% Desiccated powdered, liver
- 5.28% 1-methyl-2-(p-chlorostyryl)-pyridinium resinate
- 2.95% Diethylcarbamazine resinate
- 30.00% Microcrystalline cellulose
- 7.00% Stearic acid
  Resin particle size <147μ,
- 8% Sulfonic acid-divinylbenzene cross linkage H = 
- 36.52% Brewer's yeast
- 18.00% Desiccated powdered, liver
- 5.30% 1-methyl-2-(p-chlorostyryl)-pyridinium resinate
- 3.18% Diethylcarbamazine resinate
- 30.00% Microcrystalline cellulose
- 7.00% Stearic acid
  Average resin particle size 45μ
- 4% Sulfonic acid-divinylbenzene cross linkage From the above data it can be seen that formulation B, which contains approximately 55% by weight of liver, is most aggressively accepted by dogs. Formulation A, containing approximately 18% by weight of Brewer's yeast and 40% by weight of liver is the next most palatable formulation, and formulation C, containing about 18% by weight of liver and 40% by weight of Brewers yeast is the third most palatable formulation to the dogs. All these formulations were most palatable than the commercial Filarabit (diethylcarbamazine) formulation. Formulation F, G and H were all readily acceptable to the test dogs and were equivalent in palatability ratings. In all cases, most dogs ate both tablets as treats within 1 minute. The use of about 20% liver or more improves the rate of acceptance primarily by beneficial olfactory stimulation.

EXAMPLE 7

Palatability evaluation of styrylpyridinium-diethylcarbamazine edible tablets

The test described in example 6 above is repeated using 20 to 60 pound mongrel dogs. Tablets A, B, C and D, described in example 6, are evaluated in this test along with three different formulations designated I, J and K. The latter formulations have the following compositions:

| | | |
|---|---|---|
| I = | 18.18% | Desiccated liver powder |
| | 36.36% | Brewer's yeast |
| | 30.10% | Microcrystalline cellulose |
| | 5.28% | 1-methyl-2-(p-chlorostyryl)-pyridinium resinate |
| | 3.08% | Diethylcarbamazine citrate (no resin) |
| | 7.00% | Stearic acid |
| J = | 46.36% | Brewer's yeast |
| | 8.18% | Desiccated liver powder |
| | 30.49% | Microcrystalline cellulose |
| | 5.05% | 1-methyl-2-(p-chlorostyryl)-pyridinium resinate |
| | 2.92% | Diethylcarbamazine resinate |
| | 7.00% | Stearic acid |
| K = | 54.54% | Brewer's yeast |
| | 30.49% | Microcrystalline cellulose |
| | 5.05% | 1-methyl-2-(p-chlorostyryl)-pyridinium resinate |
| | 2.92% | Diethylcarbamazine resinate |
| | 7.00% | Stearic acid |

As in example 6, the tablets are offered to each dog twice daily for five days. Preference for formulations is reported as % consumed first.

First Preference test Results
Styrylpyridinium-Diethylcarbamazine formulations

| Formulation | | % liver | % yeast | % consumed first |
|---|---|---|---|---|
| A | | 36.36 | 18.18 | 56.4 |
| C | | 18.18 | 36.36 | 43.6 |
| A | | 36.36 | 18.18 | 41.0 |
| B | | 54.55 | 0 | 59.0 |
| B | | 54.55 | 0 | 66.0 |
| D | (Filaribits) | — | — | 34.0 |
| C | | 18.18 | 36.36 | 67.0 |
| I = | Nonresinated Diethylcarbamazine Styrylpyridinium resinate | 18.18 | 36.36 | 33.0 |
| J | | 8.18 | 46.36 | 56 |

-continued

First Preference test Results
Styrylpyridinium-Diethylcarbamazine formulations

| Formulation | % liver | % yeast | % consumed first |
|---|---|---|---|
| K | 0 | 54.54 | 44 |

From the above data it can be seen that the formulation prepared with about 54.55% liver was the most preferred formulation, However, formulations A, B and C, were all acceptable and preferred over the commercial "Filaribits" diethylcarbamazine formulation. Thus it is apparent that styrylpyridinium resinate-diethylcarbamazine resinate formulations containing 20% to 60% by weight of liver and 0–40% by weight of yeast are more acceptable i.e. palatable to dogs than the presently offered commercial preparations. The formulation containing non-resinated diethylcarbamazine was not well accepted nor were the formulations containing 0 to 9% by weight of liver.

EXAMPLE 8

Palatability Evaluation of *Styrylpyridinium *Diethylcarbamazine edible tablets

Twenty-five to 29 privately-owned pet dogs representing a variety of ages, bodyweights, breeds and both sexes were used in a series of 3 day acceptance studies. STYRID-CARICIDE Tablets to provide therepeutic levels of styrylpyridinium and diethylcarbamazine for a 20 lb. dog were formulated with a variety of liver contents and resinated or non resinated active drug components. The formulation used (A thru K) were specified in Examples 6 and 7 as follows:

| Formulation | % Liver | % Yeast | Drugs |
|---|---|---|---|
| A | 36.36 | 18.18 | CARICIDE Resinate STYRID Resinate |
| B | 54.55 | 0 | CARICIDE Resinate STYRID Resinate |
| C | 18.18 | 36.36 | CARICIDE Resinate STYRID Resinate |
| I | 18.18 | 36.36 | CARICIDE Citrate STYRID Resinate |
| J | 8.18 | 46.36 | CARICIDE Resinate STYRID Resinate |
| K | 0 | 54.54 | CARICID Resinate STYRID Resinate |

*Styrylpyridinium = STYRID
*Diethylcarbamazine = CARICIDE

*Styrylpyridinium=STYRID *Diethylcarbamazine=CARICIDE

One additional formulation to be designated formulation "L" using about 20% liver, 40% yeast with CARICIDE resinate as the only active drug was also evaluated as was Diroform ®, an edible formulation of diethylcarbamazine made by Vet-A-Mix, Inc., Shenandoah, Iowa.

Whole or parts of tablets were offered free-choice appropriate to the individual dogs body weight once daily for 3 consecutive days. A period of about 2 weeks separated each 3 day test. Acceptance of each formulation was calculated as the percentage of the total number of daily tablet presentations which were readily consumed by the dogs. If less than the entire daily dosage was accepted, then that day was considered a rejection of medication. Results are listed below:

| Formulation | % Liver | % Yeast | % Acceptance |
|---|---|---|---|
| K | 0 | 54.54 | 61 |
| J | 8.18 | 46.36 | 80 |
| C | 18.18 | 36.36 | 96 |
| A | 36.36 | 18.18 | 96 |
| B | 54.55 | 0 | 96 |
| I | 18.18 | 36.36 | 76 |
| L | about 20 | about 40 | 89 |
| Diroform | — | — | 79 |

All resinates were made using a resin of 300–800μ particle size with 4% divinylbenzene cross linkage. An excellent acceptance was attained with liver present at a concentration of about 20% or greater. Relatively poor acceptance was observed at about 10% or less liver content. A relatively low acceptance rate was seen for the now resinated diethylcarbamazine formulation (I) which was nearly equivalent to that observed for Diroform a potentially competitive product. When diethylcarbamazine resinate alone was incorporated into the 20% liver matrix it compared very favorably with the non-resinated diethylcarbamazine formulation.

EXAMPLE 9
Sequentially Loaded
Styrylpyridinium-Diethylcarbamazine Resin

DOWEX® 50W, sulfonated polystyrene-divinylbenzene cross-linked acidic resin, 3000 g is placed in a 10 l. graduated cylinder. Styrylpyridinium chloride (510.5 g) is then dissolved in 1200 ml of deionized water and 300 ml of methanol and added to the DOWEX 50W resin. The mixture is stirred for 2 hours and then permitted to settle and the acidic supernatant liquid decanted. The remaining styrylpyridinium resinate is washed 3 times with deionized water, then permitted to settle and the supernatant liquid separated from the resinate. Diethylcarbamazine base (306.3 g) is then added to the resinate and sufficient deionized water added to adjust the volume of the mixture to 11 l. The resulting mixture is stirred for 2 hours until the diethylcarbamazine is loaded on the resin along with the styrylpyridinium. The mixture is washed several times and until the final wash and resin mixture has a pH of 4.30. The supernatant liquid is separated from the styrylpyridinium-diethylcarbamazine resinate which is then dried and ready for use in preparation of the edible tablets.

The above procedures are repeated using POWDEX Resin (IR 120) ground to 45μ (2820 g). The styrylpyridinium chloride (501. g) is the first drug to be loaded on the resin as described above. This is accomplished in a methanol water solution. The resin is washed three times with deionized water and the supernatant liquid decanted. Diethylcarbamazine (291. g) is then sequentially loaded onto the washed styrylpyridinium resinate and stirred for 17 hours. The mixture is permitted to settle, the supernatant liquid decanted and the remaining resinate washed with deionized water until the pH of the wash water mixture is about 1.7.

EXAMPLE 10
Preparation of Styrylpyridinium-Diethylcarbamazine edible tablets using sequentially loaded resin Styrylpyridinium-diethylcarbamazine sequentially loaded resinate (355.4 g) is admixed with 800 g of desiccated powdered liver, 1200 g of microcrystalline cellulose (AVICEL PH102); 1362.6 g of Brewers yeast; 2.0 g of silicon dioxide and 280. g of stearic acid. The composition, thus prepared, contained 8.885% by weight of the resinated drug, 20% by weight of liver, 30% by weight of microcrystalline cellulose, 34.065% by weight of the yeast, 0.05% by weight of the silicon dioxide and 7.0% by weight of the stearic acid.

The composition is compressed into chewable 2.2 g tablets having a Kilopond hardness rating of about 8.5 Kp. The palatability of the thus prepared tablets is excellent.

EXAMPLE 11
Diethylcarbamazine Edible Tablet Palatability
Evaluations using privately owned dogs maintained under Home Environment Conditions In this study, heartworm (*Dirofilaria immitis*) negative dogs representing a random variety of breeds, ages, body weights, and both sexes, are offered diethylcarbamazine edible tablets prepared as described in example 3 above. The medicated edible tablets were offered to each dog once a day for 30 consecutive days.

Each dog is rated according to the number of acceptances as a percentage of the total number of daily presentations using the following classifications criteria:

| Rating | Acceptance |
|---|---|
| Excellent | Accepted 90% or more of the daily doses |
| Good | Accepted 89% to 75% of the daily doses |
| Fair | Accepted 74% to 51% of the daily doses |
| Poor | Accepted 50% or less of the daily doses |

Tablets are presented at the owner's convenience, usually prior to or during a meal. The acceptability panel was made up of 37 dogs representing a random variety of breeds, both sexes, a body weight range of 4.5 to 55.4 kg, and an age range of 6 months to 12.5 years as shown in table I. Acceptability results are shown in Table II, and are summarized below:

| Rating | Number of Dogs | % of Total Panel |
|---|---|---|
| Excellent | 30 | 81 |
| Good | 2 | 5 |
| Fair | 0 | 0 |
| Poor | 5 | 14 |

"Excellent" to "Good" acceptance was observed for 86% of the panel members and "Fair" to "Poor" acceptance for 14% of the panel. In general, acceptance or rejection of the tablets was not a function of the method of administration, i.e. as a treat vs. mixed with food. If the tablets were consistently rejected, the test, while still reported, was terminated for that individual prior to completion of the full test period. Throughout the trial, only one dog, was "sick". This occurred on the twenty-first day of medication and lasted for one day only. This dog was continued on medication for an additional 12 days (total of 42 days of treatment), with no adverse effects noted. Two of the smaller dogs preferred the tablets broken into pieces, but when broken, accepted them well.

TABLE I

Acceptability Panel Composition

| Breed | Males | Females | Age (Range) | Body Weight (Range in kg) |
|---|---|---|---|---|
| Borzoi | 1 | 1 | 2.5–3.5 yr. | 31.5–55.5 |
| Collie | | 1 | 13 months | 27.5 |
| Dachshund | 1 | 3 | 3–10 years | 6.0–8.0 |
| German Shepherd | | 1 | 2.5 years | 29.5 |
| G.S.H. Pointer | | 1 | 6 months | 18.0 |
| Golden Retriever | | 2 | 1.5–6 years | 29.5–32.0 |
| Irish Setter | 1 | | 8 months | 27.5 |
| Labrador Retriever | 1 | 2 | 11 months–5 years | 31.0–36.5 |
| Miniature Poodle | | 1 | 12.5 years | 8.0 |
| Miniature Schnauzer | 3 | 2 | 1–10 years | 4.5–9.0 |
| Shetland Sheepdog | 1 | | 1.5 years | 7.0 |
| Standard Poodle | | 1 | 3 years | 26.0 |
| Welch Corgi | 2 | 3 | 5–11 years | 7.5–13.5 |
| West Highland White Terrier | 1 | | 2 years | 8.5 |
| Mixed | 4 | 4 | 1.5–8 years | 8.5–45.5 |
| Totals | 15 | 22 | Range: 6 months to 12.5 years | Range: 4.5 to 55.4 kg |

TABLE II

Dog Acceptance Information and Owners Comments

| Breed | Age | Sex[1] | Days Accepted | Days Rejected | % of Presentations Accepted | How Given | Comments |
|---|---|---|---|---|---|---|---|
| Irish Setter | 8 mo. | M | 30 | 0 | 100 | Treat | Loved it |
| German Shepherd | 2.5 yr. | F | 45 | 0 | 100 | Treat | Ate it |
| Schnauzer | 1 yr. | F | 31 | 0 | 100 | Treat | Quick Acceptance |
| Schnauzer | 7 yr. | M | 31 | 0 | 100 | Treat | Quick Acceptance |
| Schnauzer | 10 yr. | M | 27 | 4 | 87 | Treat | Occasionally crumbled prior to presentation |
| Schnauzer | 5 yr. | M | 24 | 7 | 77 | Treat | Occasionally crumbled tablet or combined with food |
| Collie Mix | 3 yr. | M | 31 | 0 | 100 | Treat | Readily accepted tablet, may be too hard |
| Mix | 7 yr. | M | 33 | 0 | 100 | Treat | Enthusiastically Received |
| Schnauzer | 4 yr. | F | 31 | 0 | 100 | Treat | No adverse effects |
| Corgi | 5 yr. | F | 31 | 0 | 100 | Treat | Excellent |
| Corgi | 5 yr. | M | 31 | 0 | 100 | Treat | Good |
| Corgi | 7 yr. | F | 30 | 0 | 100 | Treat | Excellent |
| Corgi | 11 yr. | F | 31 | 0 | 100 | Treat | Excellent |
| Corgi | 6 yr. | M | 31 | 0 | 100 | Treat | Excellent |
| Collie | 13 mo. | F | 31 | 0 | 100 | Treat | Some day-to-day variation in acceptance-mostly excellent |
| Mix | 2 yr. | F | 8 | 20 | 28 | Treat | Usually didn't want it |
| Terrier Mix | 4 yr. | M | 9 | 22 | 29 | Treat or with food | Accepted only by accident |
| Mix | 6 yr. | F | 1 | 9 | 10 | Treat or with food | None |
| Mix | 1.5 yr. | M | 1 | 30 | 3 | Treat or with food | Not like the taste or consistency |
| Borzoi | 2.5 yr. | F | 30 | 0 | 100 | Treat | No adverse effects |
| Mix | 7.5 yr. | F | 30 | 0 | 100 | Treat | No adverse effects |
| Borzoi | 3.5 yr. | M | 30 | 0 | 100 | Treat | No adverse effects |
| Labrador | 17 mo. | M | 30 | 0 | 100 | Treat | Excellent-swallows them quickly |
| Labrador | 5 yr. | F | 31 | 0 | 100 | Treat | Comes running for them |
| Pointer | 6 mo. | F | 41 | 1 | 98 | Treat or with food | Never refused - either way presented |
| Labrador | 11 mo. | F | 42 | 0 | 100 | Treat or with food | Never refused - either way presented |
| Shetland Sheepdog | 1.5 yr. | M | 15 | 0 | 100 | Treat | None |
| Dachshund | 3 yr. | M | 31 | 0 | 100 | Treat or with food | None |
| Dachshund | 7 yr. | F | 31 | 0 | 100 | Treat or with food | None |
| Dachshund | 10 yr. | F | 31 | 0 | 100 | Treat or with food | None |
| Golden Retriever | 1.5 yr. | F | 31 | 0 | 100 | Treat | None |

TABLE II-continued
Dog Acceptance Information and Owners Comments

| Dog | | | Days | Days | % of Presentations | How | |
|---|---|---|---|---|---|---|---|
| Breed | Age | Sex[1] | Accepted | Rejected | Accepted | Given | Comments |
| Golden Retriever | 6 yr. | F | 25 | 1 | 96 | Treat | Excellent |
| W.H.W. Terrier | 2 yr. | M | 29 | 2 | 94 | Treat or with food | Good |
| Miniature Poodle | 12.5 yr. | F | 30 | 1 | 97 | Treat | Well accepted |
| Standard Poodle | 3 yr. | F | 31 | 0 | 100 | Treat | Well accepted |
| Mix | 8 yr. | F | 0 | 3 | 0 | Treat or with food | None |
| Dachshund | 4 yr. | F | 30 | 0 | 100 | Treat | None |

Edible Tablet Composition

| Ingredient | % Composition |
|---|---|
| 1. Diethylcarbamazine Resinate* | 3.063 |
| 2. Silicon dioxide, colloidal | 0.05 |
| 3. Brewer's Yeast | 39.887 |
| 4. Cellulose, microcrystalline | 30.0 |
| 5. Stearic Acid, powder USP | 7.0 |
| 6. Liver, dessicated (granular) | 20.0 |
| Total: | 100.0% |

Mean tablet weight: 2.232 g.
Assay: 2.75% w/w as DEC citrate

EXAMPLE 12

Palatability Evaluation of Diethylcarbamazine Edible Tablets

The following test was conducted to determine what effect 0% to 7% stearic acid has on the palatability of the chewable tablets of the present invention.

Nine sexually mature beagle dogs were demonstrated to be heartworm (*Dirofilaria immitis*) free and housed such that each dog could be tested individually. Three two-day phases of testing were performed. At least one day with no presentations was allowed between phases. On each of the two successive test days, two presentations (a.m. and p.m.) of two tablet formulations were made to each dog. The tablets were positioned about six inches apart on the floor with their relative positions reversed at each successive presentation. Approximately two minutes were allowed for the dogs to voluntarily accept (eat) or reject the tablet(s). Records were maintained for each tablet formulation, presentation, and dog to reflect tablet acceptance or rejection. The percentage of the total number of tablet presentations which were accepted were calculated for each formulation.

The tablets used in these evaluations had the following compositions:

1. Conventional diethylcarbamazine tablets containing *non-resinated* diethylcarbamazine citrate 50 mg per tablet.

2. Diethylcarbamazine resinate plus binder.

These tablets are prepared by blending diethylcarbamazine resinate (16.4 g 8.28% W/W), prepared as described in Example 1 above, with microcrystalline cellulose (483.6 g 96.8% W/W). The blended mixture is slugged, milled and compacted on a commercial tableting machine to give ¾-inch round tablets weighing 1.95 g.

3. Diethylcarbamazine resinate tablet 0% stearic acid

These tablets are prepared in accordance with Examples 1 and 3 above. Diethylcarbamazine resinate (16.4 g 3.28% W/W) is blended with minus 16 mesh desiccated liver (135 g 27.0%), microcrystalline cellulose (150.0 g 30.0% W/W) and minus 30 mesh Brewer's yeast (198.6 g 39.72% W/W). The blended materials are then formed into ¾-inch round tablets using the commercial tableting machine referred to above. The tablets weigh 2.27 g and contain *no* stearic acid.

4. Diethylcarbamazine resinate tablet containing 7% stearic acid

These tablets are prepared in the same manner as described above excepting that they contain diethylcarbamazine resinate 3.06% W/W, microcrystalline cellulose 30.0% W/W, desiccated liver 20.0% W/W, silicon dioxide 0.05% W/W, Brewer's yeast 39.89% W/W and stearic acid 7.0% W/W.

Test Formulations Compared for Palatability in Phase I, Phase II and Phase III Evaluations A. Phase I 1. Conventional, non-resinated diethylcarbamazine tablets.
3. Edible tablet: Diethylcarbamazine resinate—0% stearic acid.
   Diethylcarbamazine resinate: 3.28%
   Microcrystalline cellulose: 30.0%
   Liver, desiccated granular: 27.0%
   Brewer's yeast: 39.72%

B. Phase II

2. Diethylcarbamazine resinate—binder
   Diethylcarbamazine resinate: 3.28%
   Microcrystalline cellulose: 96.72%
3. Edible tablet: Diethylcarbamazine resinate—0% stearic acid.
   Diethylcarbamazine resinate: 3.28%
   Microcrystalline cellulose: 30.0%
   Liver, desiccated granular: 27.0%
   Brewer's yeast: 39.72%

C. Phase III

4. Edible tablet: Diethylcarbamazine resinate—7% stearic acid
   Diethylcarbamazine resinate: 3.06%
   Microcrystalline cellulose: 30.0%
   Liver, desiccated granular: 20.0%
   Brewer's yeast: 39.89%
   Silicon dioxide: 0.05%

Stearic acid: 7.0%
3. Edible Tablet: Diethylcarbamazine resinate—0% stearic acid
Diethylcarbamazine resinate: 3.28%
Microcrystalline cellulose: 30.0%
Liver, desiccated granular: 27.0%
Brewer's yeast: 39.72%

The edible tablet listed as formulations 3 and 4 in Phase I, II and III, evaluations are compositions of the present invention. The total number of presentations of each formulation in each phase is 36 (nine dogs of four presentations per dog). The acceptance calculations are as follows:

| Phase/Formulation: | | No. Presentations | No. Acceptances | % Accepted |
|---|---|---|---|---|
| Phase I: | 1. Conventional Tablet | 36 | 0 | 0 |
| | 3. Edible Tablet (0% Stearic Acid) | 36 | 23 | 64 |
| Phase II: | 2. Tablet of Resinate and Binder | 36 | 1 | 3 |
| | 3. Edible Tablet (0% Stearic Acid) | 36 | 25 | 69 |
| Phase III. | 4. Edible Tablet (7% Stearic Acid) | 36 | 29 | 80 |
| | 3. Edible Tablet (0% Stearic Acid) | 36 | 29 | 80 |

Conclusions:
A. The edible tablet is far superior to a conventional tablet (reference Phase I).
B. The edible tablet matrix is essential over and above the use of a resinate for good acceptance, as the resinate/-binder only tablet was poorly accepted (reference Phase II).
C. There is no effect on palatability (acceptance) related to the concentration of stearic acid between 0 and 7% of the total tablet weight (reference Phase III results).

I claim:
1. A palatable anthelmintic resinate composition comprising from 2% to 5% by weight of a resinated N,N-dialkylpiperazine carboxamide compound having the structural formula:

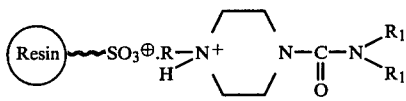

where R is hydrogen or alkyl $C_1$–$C_6$ and $R_1$ is alkyl $C_1$–$C_5$ and wherein the resin is a high capacity sulfonic cationic exchange resin of the polystyrene-divinylbenzene type having a particle size of less than 800μ; from 0 to 7% by weight of a resinated styrylpyridinium compound having the structural formula:

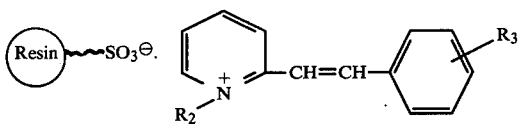

wherein $R_2$ is alkyl $C_1$–$C_4$, $R_3$ is hydrogen or halogen and the resin is a high capacity sulfonic cationic exchange resin of the polystyrene-divinylbenzene type having a particle size of less than 800μ; 18% to 60% by weight of desiccated liver; 0 to 40% by weight of Brewer's yeast; 23.95% to 31% by weight of microcrystalline cellulose, 0% to 7% by weight of stearic acid; and 0% to 0.05% by weight of sodium aluminum silicate or silicon dioxide.

2. The composition according to claim 1 wherein the resin has an average particle size range between 45μ and 300μ.

3. A method for controlling helminthiasis in companion animals comprising administering to said animals one to four, 2 gram chewable tablets daily, said tablets containing, as the essential ingredients, from 2% to 5% by weight of resinated diethylcarbamazine wherein the resin is a high capacity sulfonic cationic exchange resin of the polystyrene-divinylbenzene type; from 0% to 7% by weight of a resinated compound having the structural formula:

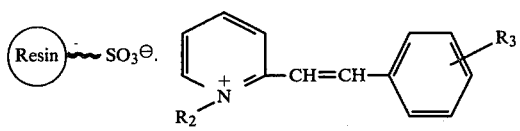

wherein $R_2$ is alkyl $C_1$–$C_4$, $R_3$ is hydrogen or halogen and the resin is a high capacity sulfonic cationic exchange resin of the polystyrene-divinylbenzene type; 18% to 60% by weight of desiccated liver; from 0% to 40% by weight of Brewer's yeast; 23.95% to 31% by weight of microcrystalline cellulose; 0% to 7% by weight of stearic acid and 0% to 0.05% by weight of sodium aluminum silicate or silicon dioxide.

4. A method for controlling helminthiasis in companion animals comprising administering to said animals one to four, 2 gram chewable tablets daily, said tablets containing, as the essential ingredients, from 2% to 5% by weight of resinated diethylcarbamazine wherein the resin is a high capacity sulfonic cationic exchange resin of the polystyrene-divinylbenzene type; 3% to 7% by weight of 1-methyl-2-(p-chlorostyryl)-pyridinium resinate, wherein the resin is a high capacity sulfonic cationic exchange of the polystyrene-divinylbenzene type; and 18% to 60% by weight of desiccated liver; from 0% to 40% by weight of Brewer's yeast; 23.95% to 31% by weight of microcrystalline cellulose; 0% to 7% by weight of stearic acid and 0% to 0.05% by weight of sodium aluminum silicate or silicon dioxide.

* * * * *